(12) United States Patent
Radhakrishnan

(10) Patent No.: US 9,186,338 B2
(45) Date of Patent: Nov. 17, 2015

(54) SOLUBILITY ENHANCER AND USE THEREOF

(76) Inventor: Ramachandran Radhakrishnan, Bangalore (IN)

( * ) Notice: Subject to any disclaimer, the term of this patent is extended or adjusted under 35 U.S.C. 154(b) by 586 days.

(21) Appl. No.: 12/067,738

(22) PCT Filed: Sep. 22, 2006

(86) PCT No.: PCT/IN2006/000390
§ 371 (c)(1),
(2), (4) Date: Jul. 7, 2008

(87) PCT Pub. No.: WO2007/034511
PCT Pub. Date: Mar. 29, 2007

(65) Prior Publication Data
US 2008/0269355 A1    Oct. 30, 2008

(30) Foreign Application Priority Data

Sep. 22, 2005 (IN) .......................... 1345/CHE/2005

(51) Int. Cl.
*A61K 31/16* (2006.01)
*A61K 47/18* (2006.01)

(52) U.S. Cl.
CPC ................. *A61K 31/16* (2013.01); *A61K 47/18* (2013.01)

(58) Field of Classification Search
CPC ........................................... A61K 31/16
USPC .......... 504/116, 785, 786, 975, 937; 424/405, 424/455, 456; 514/183
See application file for complete search history.

(56) References Cited

U.S. PATENT DOCUMENTS

| | | | |
|---|---|---|---|
| 5,099,030 A | | 3/1992 | Gardner et al. |
| 5,283,229 A | * | 2/1994 | Narayanan et al. ........... 504/365 |
| 5,645,856 A | * | 7/1997 | Lacy et al. .................... 424/455 |
| 5,859,279 A | | 1/1999 | Bannister et al. |
| 6,592,899 B2 | * | 7/2003 | Fowers et al. ................. 424/486 |
| 2007/0293550 A1 | * | 12/2007 | Rochling et al. .............. 514/361 |

FOREIGN PATENT DOCUMENTS

| | | | |
|---|---|---|---|
| JP | 62-215537 | * | 9/1987 |
| WO | WO 88/02216 | * | 4/1988 |

* cited by examiner

*Primary Examiner* — Yong Chong
(74) *Attorney, Agent, or Firm* — Knobbe, Martens, Olson & Bear LLP

(57) ABSTRACT

Disclosed herein is a novel solubility enhancer capable of being employed in formulating safe and effective pharmaceutical formulations of partially soluble drugs, wherein the solubility enhancer is selected from dialkyl substituted amides of fatty acids having $C_6$ to $C_{16}$ carbon chain, preferably from N,N-dimethyl hexanamide, N,N-dimethyl octanamide, N,N-dialkyl decanamide, N,N-dialkyl dodecanamide or N,N-dialkyl hexadecanamide.

14 Claims, No Drawings

SOLUBILITY ENHANCER AND USE THEREOF

CROSS-REFERENCE TO RELATED APPLICATIONS

This application is the U.S. National Phase of International Application No. PCT/IN2006/000390, filed Sep. 22, 2006, which claims priority to Indian Application No. 1345/CHE/2005, filed Sep. 22, 2005.

FIELD OF THE INVENTION

This invention in general relates to a novel solubility enhancer. More particularly, the present invention provides a novel solubility enhancer N,N-dialkylamide of aliphatic carboxylic acids having $C_6$-$C_{16}$ carbon chain and use thereof to enhance the solubility, permeation and bioavailability of partially soluble drugs.

BACKGROUND OF THE INVENTION

A major problem in developing pharmaceutical formulations is the poor solubility of pharmaceutical actives in water or any other commonly used medium and the subsequent poor bioavailability. To solve this problem different approaches have been taken which include developing suspensions, solubilizing in organic solvents, using salts of the drugs, developing prodrugs and using different types of drug delivery systems. Further, the insolubility of solid drug forms in common media such as water poses a major challenge because of the resulting low bioavailability of the active ingredients.

Many methods for solubilizing drugs have been developed that are based on the use of solvents or solubility enhancers, surfactants, complexation agents, or complex drug carriers. Surfactants and complexing agents have drawbacks of toxicity, and rapid precipitation of the solubilized drugs once administered to the patient or when otherwise diluted in an aqueous environment. Complex drug carriers, such as liposomes have limited utility due to the unstable nature of the carrier particles and the preferential uptake and localization of liposomal drugs to the reticuloendothelial system, namely, the liver and spleen. Conventional Solvents and solubility enhancers can be toxic and irritating when injected into humans, such that the use of this solubilization approach is largely restricted to therapies for acute, life threatening diseases where medical experts are constantly in attendance to administer palliative treatments to counteract the adverse effects of the solvents/solubility enhancers. Water miscible solvents/solubility enhancers also possess the undesirable feature of allowing the drug to rapidly precipitate when an aqueous environment is contacted.

When the aqueous solubility of a drug candidate is inadequate to permit solution formulations, solubility enhancers are often employed to improve solubility. The use of solubility enhancers can increase the solubility by several orders of magnitude. Some commonly used solubility enhancers are propylene glycol, polyethylene glycols, ethanol and sorbitol. The addition of a co-solvent can increase solubility of hydrophobic molecules by reducing the dielectric constant of the solvent. Some problems with the use of solubility enhancers are precipitation of the drug with dilution of solvent mixture and tissue damage or pain upon injection. This dilution occurs after administration of the drug into the body. Generally polyethylene glycol (PEG) is an excipient of choice based on its good solubilization properties and overall acceptability in terms of side-effect profile. Side effect profile of PEG was discussed by Pang S, N. J in Final report on the safety assessment of polyethylene glycols (PEGs) reported in Journal of American College of Toxicology (1993), 12, 429-457.

WO 9518603 discloses the property of soluble polyvinylpyrrolidone increasing the solubility of drug without negatively affecting the adhesivity of the composition or the rate of drug delivery from the pressure-sensitive adhesive composition.

WO 03064656 discloses the biotin carboxyl carrier protein (BCCP), as a protein folding marker and protein solubility enhancer in the orientated surface capture of products of heterologously expressed genes. Methods for increasing the solubility of proteins and determining the folded state of a protein are also disclosed in this reference. In addition the nucleic acid molecule encoding the biotinylation domain of the tag moiety can be used to increase the proportion of clones in a library that express the protein of interest.

WO 03028589 discloses the polymeric compositions having improved capability of solubilizing a drug in a hydrophilic environment to form a solution, which comprises a biodegradable polyester oligomer; and biodegradable AB-type, ABA-type, or BAB-type block copolymers and method of uses thereof.

Cheng Yiyun et al., in European Journal of Medicinal Chemistry (2005), 40(12), 1390-1393 discusses the use of polyamidoamine dendrimers as solubility enhancers in the pharmaceutical preparation of Ketoprofen, wherein it states experimentally that the solubility of ketoprofen in the dendrimer solutions was proportional to dendrimer concentration.

Ming-Thau Sheu et al., in Journal of controlled release (2003), 88(3), 355-368 discusses the influence of micelle solublization by tocopheryl polyethylene glycol succinate on solubility enhancement and percutaneous penetration of estradiol. Results of this study show that the solubility of estradiol was improved in the presence of tocopheryl polyethylene glycol succinate through micellar concentration.

The present invention provides a novel solubility enhancer, which is capable to enhance the solubility of the partially soluble drugs and also avoid the limitation associated with the prior arts. Further the present invention provides an alternative method for the preparation of desirable formulations of such partially soluble drugs employing said novel solubility enhancer.

SUMMARY OF THE INVENTION

It is a principal aspect of the present invention to provide a novel solubility enhancer, which effectively enhances the solubility of the partially soluble drugs without resulting in any toxicity or other side effects.

In accordance with another aspect of the present invention, there is provided a novel solubility enhancer, wherein said enhancer is able to enhance the solubility of the partially soluble drugs, thereby achieving a uniform distribution of drugs in a delivery system and hence increasing the bioavailability of said drugs.

In accordance with another aspect of the present invention, there is provided a novel solubility enhancer, wherein said enhancer effectively works as skin permeation enhancer without any toxic effect.

In accordance with one other aspect of the present invention, there is provided a novel solubility enhancer, which is capable of being employed in formulating safe and effective pharmaceutical formulations of partially soluble drugs, wherein the solubility enhancer is selected from amides of N,N-dialkyl substituted fatty acids having $C_6$ to $C_{16}$ carbon chain.

In accordance with yet other aspect of the present invention, there is provided a novel solubility enhancer, which is capable of being employed in formulating safe and effective pharmaceutical formulations of partially soluble drugs, wherein the solubility enhancer is preferably selected from amides of N,N-dialkyl substituted fatty acids having $C_6$ to $C_8$, $C_{10}$, $C_{12}$, or $C_{16}$ carbon chain.

In accordance with yet another aspect of the present invention, there is provided a novel solubility enhancer, wherein said solubility enhancer is selected preferably from N,N-dialkylamide of aliphatic carboxylic acids having $C_6$ to $C_{16}$ carbon chain, more preferably N,N-dialkyl hexanamide, N,N-dialkyl octanamide, N,N-dialkyl decanamide, N,N-dialkyl dodecanamide, N,N-dialkyl hexadecanamide.

In accordance with yet another aspect of the present invention, there is provided a novel solubility enhancer, wherein said solubility enhancer is N,N-dialkyl hexanamide.

In accordance with yet another aspect of the present invention, there is provided a novel solubility enhancer, wherein said solubility enhancer is N,N-dialkyl octanamide.

In accordance with yet another aspect of the present invention, there is provided an effective alternative method for the preparation of desirable formulations of partially soluble drugs employing said novel solubility enhancer, thereby achieving a uniform distribution of drugs in delivery systems, which enhances bioavailability of said drugs.

In accordance with yet another aspect of the present invention, there is provided a method for determining the solubility of said drugs, wherein the method comprises incremental addition of said drugs taken from stock to said solubility enhancer, shaking the resultant in an ultrasonic bath to obtain clear solution and determining the solubility.

In accordance with yet another aspect of the present invention, there is provided a method for enhancing the solubility of said drugs, wherein the method comprises mixing said drugs into hydrophilic medium, adding a solubility enhancer into resultant mixture, shaking the resultant to obtain clear solution, wherein said solubility enhancer is N,N-dialkylamide of aliphatic carboxylic acids having $C_6$ to $C_{16}$ carbon chain, preferably selected from amides of N,N-dialkyl substituted fatty acids having $C_6$ to $C_8$, $C_{10}$, $C_{12}$ or $C_{16}$ carbon chain, more preferably N,N-dialkyl hexanamide, N,N-dialkyl octanamide, N,N-dialkyl decanamide, N,N-dialkyl dodecanamide or N,N-dialkyl hexadecanamide.

In accordance with yet another aspect of the present invention, there is provided a method for the preparation of desirable formulations of partially soluble drugs, wherein the method comprises mixing said partially soluble drugs into hydrophilic medium, adding a solubility enhancer into resultant mixture, shaking the resultant to obtain clear solution and formulating the same using pharmaceutically acceptable excipients into a desirable drug delivery system, wherein said solubility enhancer is N,N-dialkylamide of aliphatic carboxylic acids having $C_6$ to $C_{16}$ carbon chain, preferably selected from amides of N,N-dialkyl substituted fatty acids having $C_6$ to $C_8$, $C_{10}$, $C_{12}$ or $C_{16}$ carbon chain, more preferably N,N-dialkyl hexanamide, N,N-dialkyl octanamide, N,N-dialkyl decanamide, N,N-dialkyl dodecanamide or N,N-dialkyl hexadecanamide.

In accordance with still another aspect of the present invention, there is provided a novel solubility enhancer, wherein said solubility enhancer is used alone as solubilising agent or in combination with other solubilising agents to enable solubilisation of the partially soluble drugs.

DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

The present invention discloses a novel solubility enhancer capable of being employed in formulating safe and effective pharmaceutical formulations of partially soluble drugs, wherein the solubility enhancer is selected from the Diallyl substituted fatty acid amides selected from the fatty acid having $C_6$ to $C_{16}$ carbon chain, preferably N,N-dialkylamides of aliphatic carboxylic acids, more preferably N,N-dimethyl hexanamide, N,N-dimethyl octanamide, N,N-dialkyl decanamide, N,N-dialkyl dodecanamide or N,N-dialkyl hexadecanamide.

The disclosed solubility enhancer has comparatively higher ability to solubilise said partially soluble drugs than the conventionally known solubility enhancers. Upon a comparative solubility study for different partially soluble drugs, it is surprisingly found that using solubility enhancer according to present invention provides better solubility than other conventionally used solubility enhancers.

The disclosed solubility enhancer also effectively works as skin permeation enhancer. The skin permeability of required drugs can be enhanced without skin damage by employing said solubility enhancer in drug formulations. With many drugs, the rate of permeation through skin is extremely low without the use of some means to enhance the permeability to the skin. The said enhancer increases the permeation ability of drugs through a body surface while minimizing the likelihood of skin damage, irritation or sensitization.

The disclosed solubility enhancer according to the present invention is prepared by employing any conventional method.

Unless defined otherwise, all technical and scientific terms used herein have the same meaning as commonly understood by one of ordinary skill in the art to which this invention belongs.

The present invention provides an effective solubility enhancer, which is capable of enhancing the solubility of partially soluble drugs, especially useful in the production of various formulations.

The term, "drug" as defined herein means any drug used in state of art, preferably as diagnostic agents, therapeutic agents or cosmetic agents used for humans or animals. The term therapeutic agents include analgesics, anti-inflammatory agents, anthelmintics, anti-arrhythmic agents, anti-asthma agents, anti-bacterial agents, anti-viral agents, anti-coagulants, anti-depressants, anti-diabetic, anti-epileptic agents, anti-gout agents, anti-hypertensive agents, anti-malarial agents, anti-migraine agents, anti-muscarinic agents, anti-neoplastic agents, immunosuppressants, anti-protozoal agents, anti-thyroid agents, anti-tussives, anxiolytics, sedatives, hypnotics, neuroleptic agents, B-blockers, cardiac inotropic agents, corticosteroids, diuretics, anti-parkinsonism agents, gastrointestinal agents, histamine receptor antagonists, lipid regulating agents, muscle relaxants, anti-anginal agents, sex hormones, stimulants, cytokines or any combinations thereof. The term cosmetic agent includes collagen obtained from human or animal origin.

The term, "formulations" as defined herein means any formulation as pharmaceutical or cosmetic preparation containing the drug, which can be administered by any route. It also comprises pharmaceutical preparations like transdermal preparations and all drug release devices.

Further, the present invention is illustrated in detail by way of the following examples. The examples are given herein for illustration of the invention and are not intended to be limiting thereof.

EXAMPLE 1

Solubility Study of Isotretinoin

The solutions of Isotretinoin were made by incremental addition technique, i.e. by adding portions of the drug from pre-weighed stock (Isotretinoin) to known volume of the alkanamide solution and shaking in an ultrasonic bath till the solution was clear. Thereafter the second weight was recorded & solubility was determined.

Based on experiments conducted the following solubility was observed:
a. 206 mg of Isotretinoin solubilized in 1 ml of Hexanamide—20.6% w/v.
b. 139.2 mg of Isotretinoin solubilized in 1 ml of Octanamide—13.92% w/v.

EXAMPLE 2

Solubility Study of Ibuprofen

The solutions of Ibuprofen were made by incremental addition technique, i.e. by adding portions of the drug from pre-weighed stock (Ibuprofen) to known volume of the alkanamide solution and shaking in an ultrasonic bath till the solution was clear. Thereafter the second weight was recorded & solubility was determined.

Based on experiments conducted the following solubility was observed:
a. 1382 mg of Ibuprofen solubilized in 1 ml of Hexanamide—138.20% w/v. Thus, 200 mg of Ibuprofen can be solubilized in 0.1447 ml of Hexanamide.
b. 760 mg of Ibuprofen solubilized in 1 ml of Octanamide—76.0% w/v. Thus, 200 mg of Ibuprofen can be solubilized in 0.264 ml of Octanamide.

EXAMPLE 3

Solubility Study of Cyclosporine

The solutions of Cyclosporine were made by incremental addition technique, i.e. by adding portions of the drug from pre-weighed stock (Cyclosporine) to known volume of the alkanamide solution and shaking in an ultrasonic bath till solution was clear. Thereafter the second weight was recorded & solubility was determined.

Based on experiments conducted the following solubility was observed:
a. 494.60 mg of Cyclosporine solubilized in 1 ml of Hexanamide—49.46% w/v. Thus 20 mg of Cyclosporine can be solubilized in 0.040 ml of Hexanamide.
b. 312.50 mg of Cyclosporine solubilized in 1 ml of Octanamide—31.26% w/v. Thus, 20 mg of Cyclosporine can be solubilized in 0.064 ml of Octanamide.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

We claim:
1. A clear solution consisting essentially of:
   a drug that is insoluble or partially soluble in an aqueous medium used for humans or animals;
   a solubilizer, wherein said solubilizer is a single N,N-dialkylamide of an aliphatic carboxylic acid selected from the group consisting of N,N-dimethyl hexanamide, N,N-dimethyl octanamide, N,N-dimethyl decanamide, and N,N-dimethyl dodecanamide; and
   optionally a surfactant.
2. The solution according to claim 1, wherein said N,N-dialkylamide of an aliphatic carboxylic acid is N,N-dimethyl hexanamide.
3. The solution according to claim 1, wherein said N,N-dialkylamide of an aliphatic carboxylic acid is N,N-dimethyl octanamide.
4. The solution according to claim 1, wherein said partially soluble drug is selected from the group consisting of an analgesic, anti-inflammatory agent, antihelmintic, anti-arrhythmic agent, anti-asthma agent, anti-bacterial agent, anti-viral agent, anti-coagulant, anti-depressant, anti-diabetic, anti-epileptic agent, anti-gout agent, anti-hypertensive agent, anti-malarial agent, anti-migraine agent, anti-muscarnic agent, anti-neoplastic agent, immunosuppressant, anti-protozoal agent, anti-thyroid agent, anti-tussive, anxiolytic, sedative, hypnotic, neuroleptic agent, β-blocker, cardiac inotropic agent, corticosteroid, diuretic, anti-parkinsonism agent, gastrointestinal agent, histamine receptor antagonist, lipid regulating agent, muscle relaxant, anti-anginal agent, sex hormone, stimulant, cytokine, collagen and any combination thereof.
5. A method for enhancing the solubility of a drug that is insoluble or partially soluble in an aqueous medium used for humans or animals, wherein the method consists essentially of:
   mixing said drug into an aqueous a hydrophilic medium,
   adding a solubility enhancer to result in a mixture, wherein said solubility enhancer is an N,N-dialkylamide of an aliphatic carboxylic acid selected from the group consisting of N,N-dimethyl hexanamide, N,N-dimethyl octanamide, N,N-dimethyl decanamide, and N,N-dimethyl dodecanamide, and
   the mixture to obtain a clear solution according to claim 1.
6. The method according to claim 5, wherein said N,N-dialkylamide of an aliphatic carboxylic acid is N,N-dimethyl hexanamide.
7. The method according to claim 5, wherein said N,N-dialkylamide of an aliphatic carboxylic acid is N,N-dimethyl octanamide.
8. A method for preparing a formulation of a drug that is insoluble or partially soluble in an aqueous medium used for humans or animals, wherein the method consists essentially of:
   mixing said drug used for humans or animals into an aqueous medium,
   adding a single N,N-dialkylamide of an aliphatic carboxylic acid selected from the group consisting of N,N-dimethyl hexanamide, N,N-dimethyl octanamide, N,N-dimethyl decanamide, and N,N-dimethyl dodecanamide,
   shaking the mixture to obtain a clear solution according to claim 1, and
   formulating the clear solution using pharmaceutically acceptable excipients into a drug delivery system.
9. The method according to claim 8, wherein said N,N-dialkylamide of an aliphatic carboxylic acid is N,N-dimethyl hexanamide.

10. The method according to claim 8, wherein said N,N-dialkylamide of an aliphatic carboxylic acid is N,N-dimethyl octanamide.

11. The method according to claim 8, wherein said drug is selected from the group consisting of an analgesic, anti-inflammatory agent, antihelmintic, anti-arrhythmic agent, anti-asthma agent, anti-bacterial agent, anti-viral agent, anti-coagulant, anti-depressant, anti-diabetic, anti-epileptic agent, anti-gout agent, anti-hypertensive agent, anti-malarial agent, anti-migraine agent, anti-muscarnic agent, anti-neoplastic agent, immunosuppressant, anti-protozoal agent, anti-thyroid agent, anti-tussive, anxiolytic, sedative, hypnotic, neuroleptic agent, β-blocker, cardiac inotropic agent, corticosteroid, diuretic, anti-parkinsonism agent, gastrointestinal agent, histamine receptor antagonist, lipid regulating agent, muscle relaxant, anti-anginal agent, sex hormone, stimulant, cytokine, collagen and any combination thereof.

12. The clear solution of claim 1, wherein the aqueous medium is water.

13. The method of claim 8, wherein the aqueous medium is water.

14. The method of claim 5, wherein the aqueous medium is water.

\* \* \* \* \*